(12) United States Patent
O'Brien et al.

(10) Patent No.: US 6,407,303 B1
(45) Date of Patent: Jun. 18, 2002

(54) ISOMERIZATION PROCESS WITH ADSORPTIVE SEPARATION AND INTEGRATED FRACTIONAL DISTILLATION

(75) Inventors: Dennis E. O'Brien; Lynn H. Rice, both of Arlington Heights, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 09/710,627

(22) Filed: Nov. 10, 2000

(51) Int. Cl.⁷ .............................. C07C 5/13; C07C 7/12
(52) U.S. Cl. ................. 585/738; 585/734; 585/825
(58) Field of Search ................. 585/738, 734, 585/825

(56) References Cited

U.S. PATENT DOCUMENTS

| | | | |
|---|---|---|---|
| 2,471,134 A | 5/1949 | Wright | 196/100 |
| 3,201,491 A | 8/1965 | Stine et al. | 260/676 |
| 3,205,166 A | 9/1965 | Ludlow et al. | 208/310 |
| 3,510,423 A | 5/1970 | Neuzil et al. | 208/310 |
| 4,006,197 A | 2/1977 | Bieser | 260/676 MS |
| 4,036,745 A | 7/1977 | Broughton | 208/310 |
| 4,230,533 A | 10/1980 | Giroux | 203/1 |
| 5,177,295 A | 1/1993 | Oroskar et al. | 585/805 |
| 5,177,299 A * | 1/1993 | McCulloch et al. | 585/826 |
| 5,300,715 A | 4/1994 | Vora | 585/254 |

OTHER PUBLICATIONS

Gerd Kaibel; 1987; Chem Eng. Technol 10 92–98; "Distillation Columns with Vertical Partitions".*
Rudd, H. "Thermal Coupling for Energy Efficiency" *Supplement to The Chemical Engineer* p. s14–s15 Aug. 27, 1992.
Schulz, R.C. (et al.) "Lab Production" Poster Session at the $2^{nd}$ World Conference on Detergents Montreux, Switzerland Oct. 5–10, 1986.

* cited by examiner

*Primary Examiner*—Thuan D. Dang
(74) *Attorney, Agent, or Firm*—John G. Tolomei; Frank S. Molinaro; Maryann Maas

(57) ABSTRACT

Construction and operational costs of simulated moving bed adsorptive separation process units are reduced by recovering desorbent from both the extract and raffinate streams of the process in a single integrated fraction column. Both streams are fractionated to recover desorbent, which is removed at one end of a dividing wall column, while separate extract and raffinate products are removed from the other end of the column. A specific embodiment includes the use of the integrated fractionation column in an isomerization application.

9 Claims, 2 Drawing Sheets

ISOMERIZATION PROCESS WITH ADSORPTIVE SEPARATION AND INTEGRATED FRACTIONAL DISTILLATION

CROSS REFERENCE TO RELATED APPLICATION

The present application is a continuation-in-part of our prior co-pending related application U.S. application Ser. No. 09/670,159 filed Sep. 26, 2000, which is hereby incorporated by reference in its entirety.

FIELD OF THE INVENTION

The invention relates to an isomerization process involving an adsorptive separation process and an innovative fractional distillation method which reduces the cost of recovering desorbent from the effluent streams of the continuous adsorptive separation process.

BACKGROUND OF THE INVENTION

In many commercially important petrochemical and petroleum industry processes it is desired to separate closely boiling chemical compounds or to perform a separation of chemical compounds by structural class. It is very difficult or impossible to do this by conventional fractional distillation due to the requirement of numerous columns or excessive amounts of energy. The relevant industries have responded to this problem by utilizing other separatory methods which are capable of performing a separation based upon chemical structure or characteristics. Adsorptive separation is such a method and is widely used to perform these separations.

In the practice of adsorptive separation a feed mixture comprising two or more compounds of different skeletal structure is passed through one or more beds of an adsorbent which selectively adsorbs a compound of one skeletal structure while permitting other components of the feed stream to pass through the adsorption zone in an unchanged condition. The flow of the feed through the dsorbent bed is stopped and the adsorption zone is then flushed to remove nonadsorbed materials surrounding the adsorbent. Thereafter the desired compound is desorbed from the adsorbent by passing a desorbent stream through the adsorbent bed. The desorbent material is commonly also used to flush nonadsorbed materials from the void spaces around and within the adsorbent. This could be performed in a single large bed of adsorbent or in several parallel beds on a swing bed basis. However, it has been found that simulated moving bed adsorptive separation provides several advantages such as high purity and recovery. Therefore, many commercial scale petrochemical separations especially for specific paraffins and xylenes are performed using simulated countercurrent moving bed (SMB) technology.

RELATED ART

A description of the use of simulated moving bed (SMB) adsorptive separation to recover paraffins from a kerosene boiling range petroleum fraction is provided in the contents of a presentation made by R. C. Schulz et al. at the 2nd World Conference on Detergents in Montreux, Switzerland on Oct. 5–10, 1986. This shows several incidental steps in the process such as fractionation and hydrotreating. A more detailed overall flow scheme for the production of olefins from the kerosene derived paraffins is presented in U.S. Pat. No. 5,300,715 issued to B. V. Vora.

Several economic advantages are derived from the continuous, as compared to batch-wise, operation of large-scale adsorptive separation processes. Recognition of this has driven the development of simulated moving bed (SMB) adsorptive separation processes. These processes typically employ a rotary valve and a plurality of lines to simulate the countercurrent movement of an adsorbent bed through adsorption and desorption zones. This is depicted, for instance, in U.S. Pat. No. 3,205,166 to D. M. Ludlow, et al. and U.S. Pat. No. 3,201,491 to L.O. Stine et al.

U.S. Pat. No. 3,510,423 to R. W. Neuzil et al. provides a depiction of the customary manner of handling the raffinate and extract streams removed from an SMB process, with the desorbent being recovered, combined and recycled to the adsorption zone. U.S. Pat. No. 4,036,745 describes the use of dual desorbent components with a single adsorption zone to provide a higher purity paraffin extract. U.S. Pat. No. 4,006,197 to H. J. Bieser extends this teaching on desorbent recycling to three component desorbent mixtures.

U.S. Pat. No. 5,177,295 issued to A. R. Oroskar et al. describes the fractionation of a "heavy" desorbent used in the recovery of paraxylene from a mixture of aromatic hydrocarbons.

The dividing wall or Petyluk configuration for fractionation columns was initially introduced some 50 years ago by Petyluk et al. A recent commercialization of a fractionation column employing this technique prompted more recent investigations as described in the article appearing at page 14 of a supplement to *The Chemical Engineer*, Aug. 27, 1992.

The use of dividing wall columns in the separation of hydrocarbons is also described in the patent literature. For instance, U.S. Pat. No. 2,471,134 issued to R. O. Wright describes the use of a dividing wall column in the separation of light hydrocarbons ranging from methane to butane. U.S. Pat. No. 4,230,533 issued to V. A. Giroux describes a control system for a dividing wall column and illustrates the use of the control system in the separation of aromatics comprising benzene, toluene and ortho-xylene.

BRIEF SUMMARY OF THE INVENTION

The invention is an improved isomerization process involving a simulated moving bed adsorptive separation process characterized by the use of an integrated fractional distillation column to recover both the extract and raffinate products of the adsorptive separation and the desorbent in a single fractionation column. A portion of the column is divided into parallel fractionation zones with one receiving the raffinate stream and the other receiving the extract stream of the adsorptive separation zone. The desorbent in these streams is rejected into a common portion of the column for further purification. This reduces the capital and operating costs of the required separation and thus of the adsorption process.

One broad embodiment of the invention may be characterized as an isomerization process where the isomerization zone effluent is passed to a simulated moving bed adsorptive separation process comprising a bed of a selective adsorbent maintained at adsorption promoting conditions. The normal pentane and normal hexane are selectively retained on a quantity of the selective adsorbent, thus forming a raffinate stream comprising the isomerized products and the desorbent formerly present in the quantity of the selective adsorbent. The desorbent is contacted with the quantity of the selective adsorbent which has retained the normal alkanes under desorption promoting conditions to yield an extract stream comprising the normal alkanes and the desorbent compound. The extract stream is passed into a fractionation column operated at fractionation conditions and divided into at least a first and a second vertical fractionation zone, with each zone having an upper and a lower end located within the fractionation column, with the first and second fractionation zones being in open communication at their upper ends at a first end of the column and with the extract stream entering the fractionation column at an intermediate point of the first fractionation zone. The raffinate stream is passed into an intermediate point of the second fractionation zone of the fractionation column. An extract product stream is removed from a first end of the first fractionation zone and contains the normal alkanes, the first end not being in communication with the second fractionation zone and being located at the second end of the column. A raffinate product stream is removed from a first end of the second fractionation zone and contains the isomerized products, the first end not being in communication with the first fractionation zone. A desorbent stream is removed from the first end of the fractionation column.

PREFERRED EMBODIMENTS AND DETAILED DESCRIPTION

Figure 1:
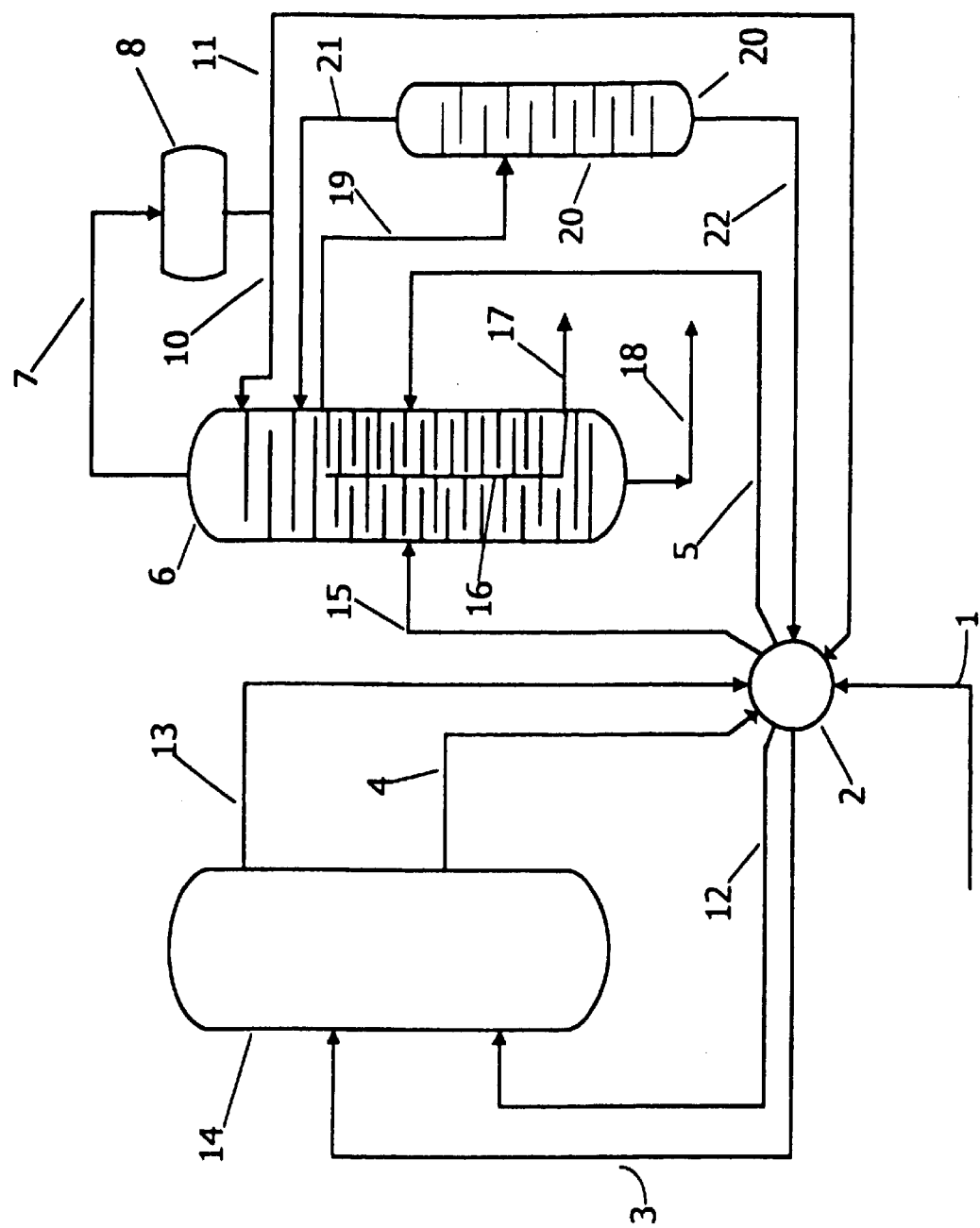
FIG. 1 is a highly simplified process flow diagram showing the extract and raffinate streams removed from the adsorbent chamber 14 being passed into different fractionation zones of a single product recovery column 6.

In many commercially important petrochemical and petroleum industry processes it is desired to separate closely boiling chemical compounds or to perform a separation of chemical compounds by structural class. Examples of this are the recovery of normal paraffins from petroleum kerosene fractions for use in the production of detergents and the recovery of paraxylene from a mixture of $C_8$ aromatics in the production of polyesters and other plastics. Meta-xylene is also recovered by adsorptive separation from xylene feed mixtures. The separation of high octane hydrocarbons from a naphtha boiling range petroleum fraction and the recovery of olefins from a mixture of paraffins and olefins are other examples of situations in which the close volatility of the compounds or the overlap in boiling points across a broad boiling range of compounds makes the use of fractional distillation impractical. For instance, in the case of the recovery of normal paraffins referred to above it is often desired to recover paraffins having a range of carbon numbers extending from about $C_9$ to $C_{12}$. This would require multiple fractional distillation columns. The resulting capital and operating costs make this approach economically unattractive.

The relevant industries have responded to this problem by utilizing other separatory methods which are capable of performing a separation based upon chemical structure or characteristics. Adsorptive separation is such a method and is widely used to perform the separations mentioned above. In adsorptive separation one or more compounds are selectively retained upon an adsorbent and then released by the application of a driving force for the desorption step. In the subject process this driving force is provided by contacting the loaded adsorbent with a desorbent compound. Therefore the adsorbent must be continuously cycled between exposure to the feed stream and a stream comprising the desorbent. As described below this forms at least two effluent streams; the raffinate stream which contains unadsorbed compounds and the extract stream containing the desired adsorbed compounds. Both streams also comprise the desorbent compound.

It is an objective of the subject invention to provide a more economical process for recovering the desorbent compound from these two streams produced during adsorptive separation. It is a specific objective of the subject invention to provide an improved simulated moving bed adsorptive separation process having reduced capital costs. These objectives are achieved by reducing the number of fractionation columns required to recover the desorbent from the extract and desorbent. A single integrated column containing parallel fractionation zones in a single column is employed instead of individual columns. Each fractionation zone occupies only a portion of the cross-section of the column, and both zones are in open communication at one end with a larger area undivided section of the column. This open communication may be at either the top or bottom end of the fractionation zones depending on whether the desorbent has a lower or higher boiling point than the raffinate and extract components of the feed.

The overall operation of the subject invention may be discerned by reference to the drawings. FIG. 1 illustrates a simulated moving bed adsorptive separation process having a single adsorbent chamber 14 and a single fractional distillation column 6. For purposes of description it is assumed that the process is being employed to separate a feed stream of line 1 comprising a mixture of several $C_8$ aromatic hydrocarbons including paraxylene, and normally also comprising meta-xylene, ortho-xylene and ethylbenzene. The very close volatilities of these compounds make it impractical to separate them on a commercial scale by fractional distillation. Therefore the predominant commercial separatory techniques are crystallization and adsorptive separation. In the process depicted in FIG. 1 the feed stream of line 1 is passed into a rotary valve 2. This rotary valve has a number of ports corresponding to the number of adsorption chamber process streams plus a "bed line" for each sub-bed of adsorbent located in the one or more adsorbent chambers used in the process. As the adsorbent chamber(s) may contain from about 8 to about 24 adsorbent sub-beds, there are a large number of bed lines involved in the process. For simplicity only those bed lines in use at the moment in time being depicted are shown on the drawing.

The rotary valve 2 directs the feed stream into bed line 3 which carries it to the adsorbent chamber 14. The feed stream enters into the adsorbent chamber at a boundary between two of the sub-beds and is distributed across the cross-section of the chamber. It then flows downward through several sub-beds of adsorbent-containing particles. The adsorbent selectively retains one compound or structural class of compound, which in this instance is paraxylene. The other components of the feed stream continue to flow downward and are removed from the adsorbent chamber in the raffinate stream carried by line 4. The raffinate stream will also comprise a varying amount of desorbent compound(s) flushed from the inter-particle void volume and removed from the adsorbent itself. This desorbent is present in the bed prior to the adsorption step due to the performance of the desorption step.

The raffinate stream enters the rotary valve 2 and is then directed into line 5. Line 5 carries the raffinate stream to a vertical fractionation zone shown occupying portions of the right-hand side of the fractional distillation column 6. This fractionation zone contains about 35–40 fractionation trays and is separated from the other fractionation zone in the column by a substantially fluid tight vertical wall 16. The vertical wall is not necessarily centered in the column. Vertical wall 16 divides a large portion of column 6 into two parallel fractionation zones. The two zones are isolated from each other for the height of this wall and also at the bottom of the wall. This seal at the bottom of the first zone distinguishes the column from a classical dividing wall column. Thus, there is no direct vapor or liquid flow between the two fractionation zones. The upper end of the fractionation zone receiving the raffinate stream of line 5 is however open to the internal volume of column 6. Thus vapor and liquid can freely move between these two portions of the column. This opening of the top of each fractionation zone into a larger fractionation zone allows vapor from both parallel zones to flow upward. The two smaller zones are thus described as being in open communication with each other and this larger zone at this point in the column. Liquid flow downward may or may not be regulated between the zones. Both of the fractionation zones have independent reboiling means (not shown). During operation, the raffinate stream entering the first fractionation zone is separated with the more volatile desorbent component(s) moving upward out of the fractionation zone and emerging into the upper portion of the column 6. The less volatile raffinate components, e.g. meta-and ortho-xylene, of the feed stream are concentrated into a bottoms stream removed from the first fractionation zone via line 17.

Simultaneously a stream of desorbent is passed into the adsorbent chamber 14 via line 12. As the desorbent moves downward through the adsorbent it removes paraxylene from the adsorbent in a section of the chamber used as the desorption zone. This creates a mixture of paraxylene and desorbent which flows through the section of the adsorbent chamber functioning as the desorption zone. This material is removed from the bottom of adsorbent chamber 14 and returned to the top of the chamber via a line (not shown) referred to in the art as the pumparound line. It flows through more adsorbent at the top of the chamber and is then removed from adsorbent chamber 14 via line 13 as the extract stream passes into the rotary valve 2. The rotary valve directs the extract stream of line 13 into line 15. Line 15 delivers the extract stream into a second vertical fractionation zone occupying a large portion of they left-hand side of column 6. The less volatile extract component, para-xylene, moves downward through the second fractionation zone and is removed from column 6 via line 18. As with the first fractionation zone, the upper end of the second zone is in open communication with the upper section of column 6, which contains additional fractionation trays extending across the entire column cross-section.

The desorbent compound(s) present in the extract stream of line 15 is driven upward in the second fractionation zone and enters the top of the column 6. The top of the column is a purification zone which is not intended for separation of extract or raffinate compounds from the desorbent. This section can be used for a separation of different desorbent components when a multicomponent desorbent stream is employed. A vapor stream comprising the desorbent component(s) is removed from the top of column 6 via line 7 and passed through an overhead condenser (not shown) to form liquid delivered to the receiver 8. A stream of liquid phase desorbent is removed from the receiver and divided into a first portion which is returned to the top of the fractionation column 6 via line 10 as reflux and a second portion which is passed through line 11 to the rotary valve 2.

The preceding description of FIG. 1 has been in terms of the use of a single component desorbent. The use of multiple component desorbents is, however, very important in some separations and is especially preferred in the separation of normal paraffins from a mixture of various other types of hydrocarbons. Using a mixture of a normal paraffin and an isoparaffin, both several carbon numbers lighter than the feed, is practiced commercially. A representative dual component mixture for the recovery of $C_{10}$–$C_{15}$ normal paraffins comprises normal pentane and iso-octane. When the subject invention is applied to a process using a dual component desorbent the integrated column can also produce a sidecut stream removed via line 19 and passed into the desorbent splitter column 20. The sidecut stream will contain all the desorbent components e.g. normal pentane and iso-octane. This sidecut stream is fed into an intermediate point in column 20, which is maintained at fractional distillation conditions which promote the separation of the lightest of the entering hydrocarbons into an overhead vapor stream removed in line 21. This overhead vapor is enriched in n-pentane and returned to an upper intermediate point of the main column 6 via line 21. The remaining iso-octane is concentrated into the net bottoms stream removed in line 22 and passed to the rotary valve 2. In this way streams rich in the separate desorbent components are delivered to the rotary valve and may be employed at different points in the desorption operation. For instance, a "zone flush" material or a bed-line flush material used in the process can be rich in iso-octane while the main desorbent stream used to remove normal paraffins from the adsorbent can be rich in n-pentane. As used herein the term "rich" is intended to indicate a concentration of the indicated compound or class of compounds greater than 50 and preferably greater than 75 mol percent.

A preferred embodiment of the invention may, therefore, be characterized as a simulated moving bed adsorptive separation process which comprises passing a feed stream comprising a first and a second chemical compound into an adsorption zone comprising a bed of a selective adsorbent maintained at adsorption promoting conditions under which the first chemical compound is selectively retained on a quantity of the selective adsorbent, thus forming a raffinate stream comprising the second chemical compound and a desorbent compound formerly present in the quantity of the selective adsorbent; passing a first desorbent stream comprising a first and a second desorbent compound into contact with the quantity of the selective adsorbent which has retained the first chemical compound under desorption promoting conditions to yield an extract stream comprising the first chemical compound and the first and second desorbent compounds; passing the extract stream into an intermediate point of a first vertical fractionation zone of a fractionation column operated at fractionation conditions and divided into at least the first fractionation zone and a substantially parallel second fractionation zone, with each zone having an upper and a lower end located within the fractionation column, with the first and second fractionation zones being in open communication at their upper end, with the fractionation column also containing an undivided fractionation section extending from the point of open communication between the first and second fractionation zones to an upper first end of the fractionation column; passing the raffinate stream into an intermediate point of the second fractionation zone of the fractionation column; removing an extract product stream from the lower end of the first fractionation zone, the first end not being in communication with the second fractionation zone; removing a raffinate product stream from a lower end of the second fractionation zone, the lower end not being in communication with the first fractionation zone; removing a second desorbent stream comprising the first desorbent compound from the first end of the fractionation column; and, removing a third desorbent stream comprising the second desorbent compound from the an intermediate point in the fractionation column located between the first end of the fractionation column and the upper end of the first fractionation zone.

Operating conditions for adsorption include, in general, a temperature range of from about 20 to about 250° C., with from about 60 to about 200° C. often being preferred. Adsorption conditions also preferably include a pressure sufficient to maintain the process fluids in the liquid phase, which may be from about atmospheric to 600 psig. Desorption conditions generally include the same temperatures and pressures as used for adsorption conditions. It is generally preferred that an SMB process is operated with an A:F flow rate through the Is adsorption zone in the broad range of about 1:1 to 5:1.0 where A is the volume rate of "circulation" of selective pore volume and F is the feed flow rate. The practice of the subject invention requires no significant variation in operating conditions, adsorbent or desorbent composition within the adsorbent chambers. That is, the adsorbent preferably remains at the same temperature throughout the process.

Although much of the description herein is set in terms of use of the invention in an SMB process, the invention is believed applicable to other modes of performing adsorptive separation such as a swing bed system employing one or more separate beds of adsorbent. The real limit to the application of the process is that the process produces two streams both comprising a single compound or group of compounds which it is desired to recover by fractionation.

Another variation in the performance of the process is the replacement of the rotary valve with a manifold system of valves. Such systems have been described in the art, e.g., U.S. Pat. No. 4,434,051, and become more practical as the number of sub-beds of adsorbent decreases. Further variation is possible concerning which of the two streams enters which fractionation zone, which is set primarily by practical engineering considerations.

Yet another variation which departs from the depiction in FIG. 1 is the instance of a separation in which the desorbent has a higher boiling point than the raffinate and extract components. In this case the desorbent is removed from the bottom of the fractionation column and both of the parallel fractionation zones would be open at the bottom and in communication with the larger section from which the desorbent is withdrawn. One of the fractionation zones is sealed at its upper end, and product removed there. The use of "heavy" desorbents, that is desorbents having higher boiling points than the raffinate or extract components of the feed, in the separation of paraxylene is described in U.S. Pat. Nos. 5,107,062; 5,057,643 and U.S. Pat. No. 5,012,038. The fractionation of a heavy desorbent from the extract and raffinate is shown in previously cited U.S. Pat. No. 5,177,295.

As different separations are performed in the two parallel separation zones the mechanical details and equipment in the two zones may differ. For instance, they may contain different types of fractionation trays, trays of the same type but at different spacing or one fractionation zone may contain or be augmented by structured packing.

The success of a particular adsorptive separation is determined by many factors. Predominant in these factors are the composition of the adsorbent (stationary phase) and desorbent (mobile phase) employed in the process. The remaining factors are basically related to process conditions.

The subject process is not believed to be limited to use with any particular form of adsorbent. The adsorbents employed in the process preferably comprise a molecular sieve such as a type A, X or Y zeolite or silicalite. Silicalite is well described in the literature. It is disclosed and claimed in U.S. Pat. No. 4,061,724 issued to Grose et al. A more detailed description is found in the article, "Silicalite, A New Hydrophobic Crystalline Silica Molecular Sieve," *Nature*, Vol. 271, Feb. 9, 1978 which is incorporated herein by reference for its description and characterization of silicalite. Silicalite is a hydrophobic crystalline silica molecular sieve having intersecting bent-orthogonal channels formed with two cross-sectional geometries, 6 Å circular and 5.1–5.7 Å elliptical on the major axis. A wide number of adsorbents are known and a starting molecular sieve is often treated by ion exchange or steaming, etc., to adjust its adsorptive properties. Adsorbents based on zeolites X and Y are described in more detail in U.S. Pat. Nos. 3,663,638; 3,626,020 and 3,997,620.

The active component of the adsorbents is normally used in the form of particle agglomerates having high physical strength and attrition resistance. The agglomerates contain the active adsorptive material dispersed in an amorphous, inorganic matrix or binder, having channels and cavities therein which enable fluid to access the adsorptive material. Methods for forming the crystalline powders into such agglomerates include the addition of an inorganic binder, generally a clay comprising a silicon dioxide and aluminum oxide, to a high purity adsorbent powder in a wet mixture. The binder aids in forming or agglomerating the crystalline particles. The blended clay-adsorbent mixture may be extruded into cylindrical pellets or formed into beads which are subsequently calcined in order to convert the clay to an amorphous binder of considerable mechanical strength. The adsorbent may also be bound into irregular shaped particles formed by spray drying or crushing of larger masses followed by size screening. The adsorbent particles may thus be in the form of extrudates, tablets, spheres or granules having a desired particle range, preferably from about 16 to about 60 mesh (Standard U.S. Mesh) (1.9 mm to 250 microns). Clays of the kaolin type, water permeable organic polymers or silica are generally used as binders. The active molecular sieve component of the adsorbents will ordinarily be in the form of small crystals present in the adsorbent particles in amounts ranging from about 75 to about 98-wt. % of the particle based on volatile-free composition. Volatile-free compositions are generally determined after the adsorbent has been calcined at 900° C. in order to drive off all volatile matter.

Those skilled in the art will appreciate that the performance of an adsorbent is often greatly influenced by a number of factors not related to its composition such as operating conditions, feed stream composition and the water content of the adsorbent. The optimum adsorbent composition and operating conditions for the process are therefore dependent upon a number of interrelated variables. One such variable is the water content of the adsorbent which is expressed herein in terms of the recognized Loss on Ignition (LOI) test. In the LOI test the volatile matter content of the zeolitic adsorbent is determined by the weight difference obtained before and after drying a sample of the adsorbent at 500° C. under an inert gas purge such as nitrogen for a period of time sufficient to achieve a constant weight. For the subject process it is preferred that the Water content of the adsorbent results in an LOI at 900° C. of less than 7.0% and preferably within the range of from 0 to 4.0 wt. %.

An important characteristic of an adsorbent is the rate of exchange of the desorbent for the extract component of the feed mixture materials or, in other words, the relative rate of desorption of the extract component. This characteristic relates directly to the amount of desorbent material that must be employed in the process to recover the extract component from the adsorbent. Faster rates of exchange reduce the amount of desorbent material needed to remove the extract component and, therefore, permit a reduction in the operating cost of the process. With faster rates of exchange, less desorbent material has to be pumped through the process and separated from the extract stream for reuse in the process. Exchange rates are often temperature dependent. Ideally, desorbent materials should have a selectivity equal to about 1 or slightly less than 1 with respect to all extract components so that all of the extract components can be desorbed as a class with reasonable flow rates of desorbent material, and so that extract components can later displace desorbent material in a subsequent adsorption step.

In adsorptive separation processes, which are generally operated continuously at substantially constant pressures and a temperature which ensures liquid phase, the desorbent material must be judiciously selected to satisfy many criteria. First, the desorbent material should displace an extract component from the adsorbent with reasonable mass flow rates without itself being so strongly adsorbed as to unduly prevent an extract component from displacing the desorbent material in a following adsorption cycle. Expressed in terms of the selectivity, it is preferred that the adsorbent be more selective for all of the extract components with respect to a raffinate component than it is for the desorbent material with respect to a raffinate component. Secondly, desorbent materials must be compatible with the particular adsorbent and the particular feed mixture. More specifically, they must not reduce or destroy the capacity of the adsorbent or selectivity of the adsorbent for an extract component with respect to a raffinate component. Additionally, desorbent materials should not chemically react with or cause a chemical reaction of either an extract component or a raffinate component. Both the extract stream and the raffinate stream are typically removed from the adsorbent void volume in admixture with desorbent material and any chemical reaction involving a desorbent material and an extract component or a raffinate component or both would complicate or prevent product recovery. The desorbent should also be easily separated from the extract and raffinate components, as by fractionation. Finally, desorbent materials should be readily available and reasonable in cost.

As indicated above, the desorbent may be a mixture of two or more compounds. For instance, a preferred desorbent for the separation of normal $C_9$–$C_{11}$ paraffins from kerosene comprises a mixture of a normal paraffin and a cycloparaffin (naphthene). A mixture in which the normal and cycloparaffins have the same carbon number is highly preferred, with carbon numbers of the desorbent compounds being in the general range of 5 to 8. The preferred normal paraffin is n-hexane, and the desorbent may range from 0 to 100% normal paraffin. The desorbent may also be 100% cycloparaffin.

Further details on equipment and techniques for use in an SMB process may be found in U.S. Pat. Nos. 3,208,833; 3,214,247; 3,392,113; 3,455,815; 3,523,762; 3,617,504; 4,006,197; 4,133,842; and 4,434,051. A different type of simulated moving bed operation which can be performed using similar equipment, adsorbent and conditions but which simulates cocurrent flow of the adsorbent and liquid in the adsorption chambers is described in U.S. Pat. Nos. 4,402,832 and 4,498,991. A more thorough explanation of simulated moving bed processes is given in the Adsorptive Separation section of the Kirk-Othmer Encyclopedia of Chemical Technology at page 563.

U.S. Pat. No. 4,992,618 issued to S. Kulprathipanja describes the use of a "prepulse" of a desorbent component in an SMB process recovering normal paraffins. The prepulse is intended to improve the recovery of the extract normal paraffins across the carbon number range of the feed. The prepulse enters the adsorbent chamber at a point before (downstream) of the feed injection point. A related SMB processing technique is the use of "zone flush." The zone flush forms a buffer zone between the feed and extract bed lines to keep the desorbent, e.g., normal pentane, from entering the adsorption zone. While the use of a zone flush requires a more complicated, and thus more costly rotary valve, the use of zone flush is preferred in the adsorption zones when high purity extract product are desired. In practice, a quantity of the mixed component desorbent recovered overhead from the extract and/or raffinate columns is passed into a separate splitter column. A high purity stream of the lower strength component of the mixed component desorbent is recovered and used as the zone flush stream. Further information on the use of dual component desorbents and on techniques to improve product purity such as the use of flush streams may be obtained from U.S. Pat. Nos. 3,201,491; 3,274,099; 3,715,409; 4,006,197 and 4,036,745 which are incorporated herein by reference for their teaching on these aspects of SMB technology.

SMB Technology has been applied to a wide variety of chemicals in addition to those described above. For instance, U.S. Pat. No. 4,467,126 describes the recovery of a di-substituted benzene such as a nitrotoluene isomer. The separation of 2,6-dimethylnaphthalene is described in U.S. Pat. No. 5,004,853 and 2,7-diisopropyinaphthalene in U.S. Pat. No. 5,012,039. SMB technology has been extended to the separation of sugars, to the separation of chiral compounds and to more complicated organics such as fatty acids and triglycerides as described in U.S. Pat. No. 5,225,580. The separation of fatty acids is described in U.S. Pat. Nos. 4,404,145; 4,770,819; 5,171,870 and 5,179,219. It is believed that the subject process can be applied to any SMB process requiring desorbent recovery. This includes the recovery of normal paraffins or slightly branched paraffins for use in the manufacture of detergents by alkylation or by conversion to alcohols or other compounds as described in Patent Publication WO 00/12451 of Mar. 9, 2000.

For purposes of this invention, various terms used herein are defined as follows. A "feed mixture" is a mixture containing one or more extract components and one or more raffinate components to be separated by the process. The term "feed stream" indicates a stream of a feed mixture which is passed into contact with the adsorbent used in the process. An "extract component" is a compound or class of compounds that is more selectively adsorbed by the adsorbent while a "raffinate component" is a compound or type of compound that is less selectively adsorbed. The term "desorbent material" shall mean generally a material capable of desorbing an extract component from the adsorbent. The term "raffinate stream" or "raffinate output stream" means a stream in which a raffinate component is removed from the adsorbent bed after the adsorption of extract compounds. The composition of the raffinate stream can vary from essentially 100% desorbent material to essentially 100% raffinate components. The term "extract stream" or "extract output stream" means a stream in which an extract material, which has been desorbed by a desorbent material, is removed from the adsorbent bed. The composition of the extract stream can vary from essentially 100% desorbent material to essentially 100% extract components.

At least portions of the extract stream and the raffinate stream are passed to separation means, typically fractional distillation columns, where at least a portion of desorbent material is recovered and an extract product and a raffinate product are produced. The terms "extract product" and "raffinate product" mean streams produced by the process containing, respectively, an extract component and a raffinate component in higher concentrations than those found in the extract stream and the raffinate stream withdrawn from the adsorbent chamber. The extract stream may be rich in the desired compound or may only contain an increased concentration. The term "rich" is intended to indicate a concentration of the indicated compound or class of compounds greater than 50 mole percent.

It has become customary in the art to group the numerous beds in the SMB adsorption chamber(s) into a number of zones. Usually the process is described in terms of 4 or 5 zones. The first contact between the feed stream and the adsorbent is made in Zone I, the adsorption zone. The adsorbent or stationary phase in Zone I becomes surrounded by liquid which contains the undesired isomer(s), that is, with raffinate. This liquid is removed from the adsorbent in Zone II, referred to as a purification zone. In the purification zone the undesired raffinate components are flushed from the void volume of the adsorbent bed by a material which is easily separated from the desired component by fractional distillation. In Zone III of the adsorbent chamber(s) the desired isomer is released from the adsorbent by exposing and flushing the adsorbent with the desorbent (mobile phase). The released desired isomer and accompanying desorbent are removed from the adsorbent in the form of the extract stream. Zone IV is a portion of the adsorbent located between Zones I and III which is used to segregate Zones I and III. In Zone IV desorbent is partially removed from the adsorbent by a flowing mixture of desorbent and undesired components of the feed stream. The liquid flow through Zone IV prevents contamination of Zone III by Zone I liquid by flow cocurrent to the simulated motion of the adsorbent from Zone III toward Zone I. The terms "upstream" and "downstream" are used herein in their normal sense and are interpreted based upon the overall direction in which liquid is flowing in the is adsorbent chamber. That is, if liquid is generally flowing downward through a vertical adsorbent chamber, then upstream is equivalent to an upward or higher location in the chamber.

A PREFERRED EMBODIMENT OF THE INVENTION

One specific embodiment of the present invention involves the isomerization of $C_5$ to $C_6$ paraffins and adsorptive separation followed by integrated parallel fractionation to recover the desired high-octane isomerization products and recycle desorbent and low octane normal paraffins. The invention is not restricted to any particular type of isomerization zone or adsorption zone. The isomerization zone can consist of any type of isomerization zone that takes a stream of $C_5$ to $C_6$ straight chain hydrocarbons or a mixture of straight chain and branched chain hydrocarbons and converts straight chain hydrocarbons in the feed mixture to branched chain hydrocarbons and branched chain hydrocarbons to more highly branched hydrocarbons thereby producing an effluent having branched chain and straight chain hydrocarbons. The adsorption section is preferably liquid phase and can utilize any type of well known adsorption process such as swing bed, simulated moving bed or other schemes for contacting the adsorbent with the feed mixture and desorbing the feed mixture from the adsorbent with the desorbent material.

Suitable feedstocks for this specific embodiment will include $C_5$ and $C_6$ hydrocarbons, and will include at least normal hexane and normal pentane. The typical feed for this process will be a naphtha feed with an initial boiling point in the range of normal butane. The feedstocks that can be used for this invention include hydrocarbon fractionations rich in $C_4$ to $C_6$ normal paraffins. The term "rich" is defined as having a stream having more than 50% of the mentioned component. Useful feedstocks include light natural gasoline, light straight-run naphtha, gas oil condensates, light raffinates, light reformate, light hydrocarbons, and straight-run distillates having distillation end points of about 77° C. (170° F.) and containing substantial quantities of $C_4$ to $C_6$ paraffins. The feed may also contain low concentrations of unsaturated hydrocarbons and hydrocarbons having more than six carbon atoms. The concentrations of these materials should be limited to 10 wt. % for unsaturated compounds and 20 wt. % for heavier hydrocarbons in order to restrict hydrogen consumption in cracking reactions. The feeds in any normal paraffin recycle are combined and typically enter the isomerization zone with a hydrogen stream.

This specific embodiment is described with reference to FIG. 2. Reference to the specific arrangement for this invention for the specific embodiment of the invention is not meant to limit the scope to the details disclosed therein. Furthermore, FIG. 2 is a schematic illustration and does not show a number of details for the process arrangement such as pumps, compressors, valves, stabilizers and recycle lines which are well known to those skilled in the art.

Hydrogen is admixed with the feed to the isomerization zone in an amount that will provide a hydrogen to hydrocarbon molar ratio of from 0.01 to 10 in the effluent from the isomerization zone. Preferably, the hydrogen to hydrocarbon molar ratio is in the range of 0.05 to 5. Although no net hydrogen is consumed in the isomerization reaction, the isomerization zone will have a net consumption of hydrogen often referred to as the stoichiometric hydrogen requirement which is associated with a number of side reactions that occur. These side reactions include saturation of olefins and aromatics, cracking and disproportionati6n. For feeds having a high level of unsaturates, satisfying the stoichiometric hydrogen will require a higher hydrogen to hydrocarbon ratio for the feed at the inlet of the isomerization zone. Hydrogen in excess of the stoichiometric amounts for the side reactions is often maintained in the reaction zone to provide stability and conversion by compensating for variation in feed stream compositions that alter the stoichiometric hydrogen requirements. Higher hydrogen to hydrocarbon ratios are often used to prolong catalyst life by suppressing side reactions such as cracking and disproportionation. When such side reactions occur, they can reduce conversion and lead to formation of carbonaceous compounds, usually referred to as coke, that foul the catalyst.

It has been found that the hydrogen to hydrocarbon ratio in isomerization zones that use a chlorided platinum alumina catalyst can be reduced significantly. In such cases, it is desirable to reduce the amount of hydrocarbon that enters the isomerization zone such that the hydrogen to hydrocarbon ratio of the effluent from the isomerization zone is less than 0.05. Reduced hydrogen to hydrocarbon ratios have been used based on the finding that the amount of hydrogen needed for suppressing coke formation need not exceed dissolved hydrogen levels. The amount of hydrogen in solution at the normal conditions of the isomerization zone effluent are preferably in a ratio of from 0.02 to 0.01.The amount of excess hydrogen over the stoichiometric requirement that is required for good stability and conversion is in a ratio of 0.01 to less than 0.05. When the hydrogen to hydrocarbon ratio exceeds 0.05, it is not economically desirable to operate the isomerization zone without the recycle of hydrogen to the isomerization zone. Hydrogen may be added to the feed mixture in any manner that provides the necessary control for the addition of the hydrogen.

Figure 2:
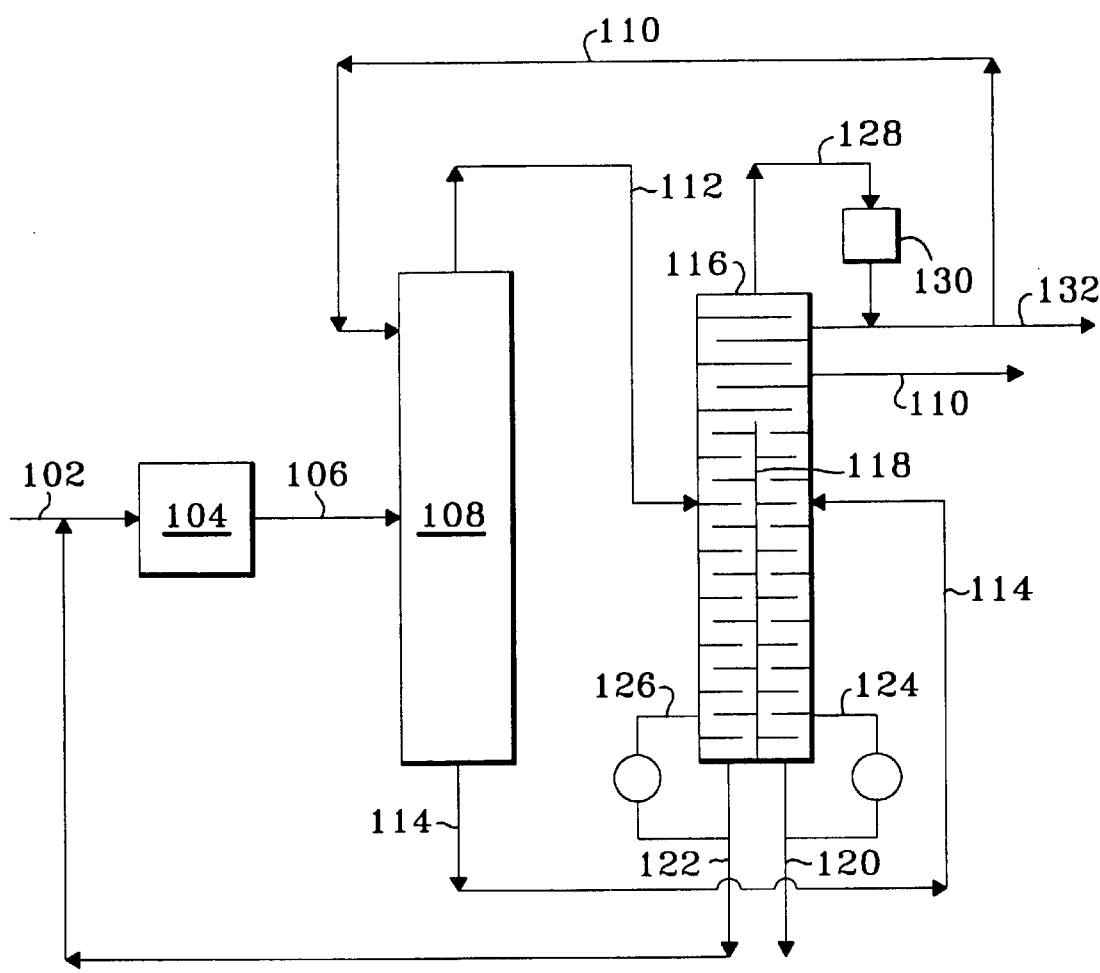
FIG. 2 is a highly simplified process flow diagram showing a specific embodiment of the invention where the invention is employed in an isomerization process.

The hydrogen and hydrocarbon feed mixture in line 102 of FIG. 2 is contacted in the isomerization zone, 104, with an isomerization catalyst. The catalyst composites that can be used in the isomerization zone include traditional isomerization catalysts. Such catalysts include high chloride catalyst on an alumina base containing platinum, and crystalline aluminosilicates or crystalline zeolites. Suitable catalyst compositions of this type will exhibit selective and bstantial isomerization activity under the operating conditions of the process.

The preferred isomerization catalyst for this invention is a chlorided platinum alumina catalyst. The alumina is preferably an anhydrous gamma-alumina with a high degree of purity. The catalyst may also contain other platinum group metals. The term "platinum group metals" refers to noble metals excluding silver and gold which are selected from the group consisting of platinum, palladium, germanium, ruthenium, rhodium, osmium, and iridium. These metals demonstrate differences in activity and selectivity such that platinum has now been found to be the most suitable for this process. The catalyst will contain from about 0.1 to 0.25 wt. % of the platinum. Other platinum group metals may be present in a concentration of from 0.1 to 0.25 wt. %. The platinum component may exist within the final catalytic composite as an oxide or halide or as an elemental metal. The presence of the platinum component in its reduced state has been found most suitable for this process. The chloride component termed in the art "a combined chloride" is present in an amount from about 2 to about 15 wt. % based on the dry support material. The use of chloride in amounts greater than 5 wt. % have been found to be the most beneficial for this process. The inorganic oxide preferably comprises alumina and more preferably gamma-alumina, eta-alumina, and mixtures thereof.

There are a variety of ways for preparing the catalytic composite and incorporating the platinum metal and the chloride therein. The method that has shown the best results in this invention prepares the catalyst by impregnating the carrier material through contact with an aqueous solution of a water-soluble decomposable compound of the platinum group metal. For best results, the impregnation is carried out by dipping the carrier material in a solution of chloroplatinic acid. Additional solutions that may be used include ammonium chloroplatinate, bromoplatinic acid or platinum dichloride. Use of the platinum chloride compound serves the dual function of incorporating the platinum component and at least a minor quantity of the chloride into the catalyst. Additional amounts of halogen must be incorporated into the catalyst by the addition or formation of aluminum chloride to or on the platinum-aluminum catalyst base. An alternate method of increasing the halogen concentration in the final catalyst composite is to use an aluminum hydrosol to form the aluminum carrier material such that the carrier material also contains at least a portion of the chloride. Halogen may also be added to the carrier material by contacting the calcined carrier material with an aqueous solution of the halogen acid such as hydrogen chloride.

It is generally known that high chlorided platinum-alumina catalysts of this type are highly sensitive to sulfur and oxygen-containing compounds. Therefore, the use of such catalysts requires that the feedstock be relatively free of such compounds. A sulfur concentration no greater than 0.5 ppm is generally required. The presence of sulfur in the feedstock serves to temporarily deactivate the catalyst by platinum poisoning. Activity of the catalyst may be restored by hot hydrogen stripping of sulfur from the catalyst composite or by lowering the sulfur concentration in the incoming feed to below 0.5 ppm so that the hydrocarbon will desorb the sulfur that has been adsorbed on the catalyst. Water can act to permanently deactivate the catalyst by removing high activity chloride from the catalyst and replacing it with inactive aluminum hydroxide. Therefore, water, as well as oxygenates, in particular $C_1$–$C_5$ oxygenates, that can decompose to form water, can only be tolerated in very low concentrations. In general, this requires a limitation of oxygenates in the feed to about 0.1 ppm or less. The feedstock may be treated by any method that will remove water and sulfur compounds. Sulfur may be removed from the feed stream by hydrotreating. A variety of commercial dryers are available to remove water from the feed components. Adsorption processes for the removal of sulfur and water from hydrocarbon streams are also well known to those skilled in the art.

As a class, the crystalline aluminosilicate or crystalline zeolite catalysts comprise crystalline zeolitic molecular sieves having an apparent pore diameter large enough to adsorb neopentane. A silica alumina molar ratio $SiO_2$:$Al_2O_3$ of greater than 3, less than 60 and preferably between 15 and 30 is desirable. In preferred form, the zeolite will contain an equivalent percentage of alkali metal cations and will have those $AlO_4$-tetrahedra not associated with alkali metal cations, either not associated with any metal cations or associated with divalent or other polyvalent metal cations. Usually the molecular sieve is a mordenite molecular sieve which is essentially in the acid form or is converted to the acid form. Particularly preferred catalysts of this type for isomerization are disclosed in detail in U.S. Pat. Nos. 3,442,794 and 3,836,597.

A preferred composition of zeolitic catalyst for use in the isomerization zone of the present invention comprises a Group VIII noble metal, a hydrogen form crystalline aluminosilicate, and a refractory inorganic oxide with the catalyst composition having a surface area of at least 580 $m^2/g$. Significant improvements in isomerization performance are realized when the surface area of the catalytic composite is at or above 580 $m^2/g$. A Group VIII metal is incorporated into the catalytic composite to supply a hydrogenation/ dehydrogenation function and the preferred Group VIII noble metal is platinum. The Group VIII noble metal is present in an amount from about 0.01 to 5% by weight of the composite and preferably in an amount of at least 0.15% by weight but not over 0.35% by weight. The zeolitic catalytic composite may also contain a catalytically effective amount of a promoter metal such as tin, lead, germanium, cobalt, nickel, iron, tungsten, chromium, molybdenum, bismuth, indium, gallium, cadmium, zinc, uranium, copper, silver, gold, tantalum, or one or more of rare earth metals and mixtures thereof. The hydrogen-formed silica alumina has either a three-demensional or channel pore structure crystal lattice framework. The three-demensional aluminosilicates include both synthetic and naturally occurring silica aluminas such as faujasites, which include X-type, Y-type, ultrastable-Y, and the like. L-type, omega-type, and mordenite are examples of the channel pore structure crystalline aluminosilicates. Mordenite, in either naturally occurring or synthetic form are preferred, particularly with a silica to alumina ratio of at least 16:1. The hydrogen form aluminosilicate may be present in an amount within the range of 50 to about 99.5 wt. %, preferably within the range of 75 to about 95 wt. %, and a refractory inorganic oxide may be present in an amount within the range of from 25 to about 50 wt. %.

Operating conditions within the isomerization zone are selected to maximize the production of isomerized products from the feed components. Temperatures within the reaction zone will usually range from about 40–320° C. (100–600° F.). Lower reaction temperatures usually favor equilibrium mixtures of isoalkanes versus normal alkanes. Lower temperatures are particularly useful in processing feeds composed of $C_5$ and $C_6$ alkanes where the lower temperatures favor equilibrium mixtures having the highest concentration of the most branched isoalkanes. When the feed mixture is primarily $C_5$ and $C_6$ alkanes, temperatures in the range of from 600 to 160° C. are preferred. Higher reaction temperatures increase catalyst activity and promote the isomerization of $C_4$ hydrocarbons. The reaction zone may be maintained over a wide range of pressures. Pressure conditions in the isomerization of $C_4$–$C_6$ paraffins range from 700 to 7000 Kpag, and preferably from 2000 to 3000 Kpag. The feed rate to the reaction zone can also vary over a wide range including liquid hourly space velocities ranging from 0.5 to 12 hr.$^{-1}$. However, space velocities between 1 and 6 hr.$^{-1}$ are preferred. The isomerization zone will usually operate at a LHSV of about 2.

Operation of the isomerization zone with the preferred chlorided platinum-alumina catalyst also requires the presence of a small amount of an organic chloride promoter. The organic chloride promoter serves to maintain a high level of active chloride on the catalyst as low levels are continuously stripped off the catalyst by the hydrocarbon feed. The concentration of promoter in the reaction zone is maintained at from 30 to 300 ppm. The preferred promoter compound is perchloroethylene. Other suitable promoter compounds include oxygen-free decomposable organic chlorides such as propyldichloride, butylchloride, and chloroform to name only a few of such compounds. The need to keep the reactants dry is reinforced by the presence of the organic chloride compound which converts to hydrogen chloride. As long as the process streams are kept dry, there will be no adverse effect from the presence of hydrogen chloride.

The isomerization zone usually includes a two-reactor system with a first stage reactor and a second stage reactor with the catalyst being distributed equally between the two reactors. It is not necessary that the reaction is carried out in two reactors but the use of two reactors confers several benefits on the process. The use of two reactors and specialized valving allows partial replacement of the catalyst system without taking the isomerization unit off stream. For the short periods of time during which replacement of catalyst may be necessary, the entire flow of reactants may be processed through only one reaction vessel while catalyst is replaced in the other. The use of two reaction zones also aids in maintaining lower catalyst temperatures. This is accomplished by having any exothermic reaction such as hydrogenation of unsaturates performed in a first reaction vessel with the rest of the reaction carried out in a final reaction vessel at more favorable temperature conditions.

The effluent from the isomerization reactors enters a stabilizer that removes light gases and butane from the effluent (not shown). The amount of butane taken off from the stabilizer will vary depending on the amount of butane entering the process. The stabilizer normally runs at a pressure of from 800 to 1700 Kpaa. When the isomerization zone is operated with a high hydrogen to hydrocarbon ratio, a separator is usually placed ahead of the stabilizer. A hydrogen-rich recycle gas stream is recovered from the separator and recycled for combination with the feed entering the isomerization zone. When the isomerization zone operates with very low hydrogen to hydrocarbon ratios the separator is not needed and the effluent from the isomerization zone may enter the stabilizer directly.

The bottoms stream from the stabilizer provides an isomerization zone effluent stream comprising $C_5$ and higher boiling hydrocarbons that include normal paraffins for recycle and branched paraffin products. The chlorides which may be present in the reaction zone will usually pose no problem for the adsorbent in the adsorption zone. In normal operation, any chlorides that are present in the effluent from the isomerization zone will be removed in the overhead from the stabilizer. However, where the isomerization zone or separators downstream from the isomerization zone are subject to upsets, it may be desirable to provide a guard bed of some type to treat the stabilizer bottoms and prevent any carryover of chloride compounds into the adsorption section.

The isomerization effluent is conducted in line 106 to the adsorption section 108 where it is contacted with a solid adsorbent in an adsorption zone. It is expected that the isomerization effluent will contain compounds such as normal pentane, normal hexane, isopentane, 2-methylpentane, 3-methylpentane, methylcyclopentane, cyclohexane, $C_7$+, isopentane, 2,2-dimethylbutane, 2,3-dimethylbutane and trace other compounds. The adsorption section of this invention is operated to primarily remove the normal pentane and normal hexane fraction from the effluent of the isomerization zone. This process is especially suited for adsorption systems that use multiple ports for supplying the process streams to the adsorbent and divide the adsorbent into a plurality of zones for adsorbing normal paraffins, recovering isoparaffins, purifying the adsorbent, and desorbing the normal paraffins. A well-known, and preferred, process of this type is the simulated countercurrent moving bed system for simulating moving bed countercurrent flow systems as described earlier. Additional details on the operation of a typical adsorption zone in an isomerization application may be found in U.S. Pat. No. 5,043,525 hereby incorporated by reference in its entirety. The specific embodiment of the invention will be discussed in terms of a simulated moving bed mode of operation.

Desorbent is introduced to adsorptive separation section 108 via line 110. For this specific embodiment, the preferred desorbent is a mixture of normal butane and isobutane. The ratio of normal butane to isobutane in a desorbent mixture preferably is in the range of from about 80:20 to about 95:5. As an option, line 110 and line 106 may be combined and fed to the adsorptive separation section 108 in combination. However, it is preferred to introduce the desorbent in a separate stream so as to control the location of the desorbent input into the simulated moving bed.

The extract stream 112 from the adsorptive separation section 108 will contain desorbent and the extract components, normal paraffins, which were selectively adsorbed by the adsorbent. Specifically normal butane, isobutane, normal pentane, and normal hexane will be present in the extract stream. The raffinate stream 114 from adsorptive separation section 108 will contain desorbent and isomerization products that were not adsorbed by the adsorbent, such as isopentane, 2-methyl pentane, 3-methyl pentane, methyl cyclopentane, cyclohexane, isopentane, 2,2,-dimethyl butane, 2,3-dimethyl butane, $C_7$+ and other trace compounds. Both the extract stream and the raffinate stream are directed to vertical fractional distillation column 116. Line 114 carries the raffinate stream to the vertical fractionation zone occupying portions of the right hand side of the fractional distillation column 116. This fractionation zone is separated from the other fractionation zone in column 116 by a substantially fluid tight vertical wall 118. The vertical wall is not necessarily centered in column 116. Vertical wall 118 divides a large portion of column 116 into two parallel fractionation zones. The upper end of the fractionation zone receiving the raffinate stream of line 114 is however open to the internal volume of column 116. Thus, vapor or liquid can freely move between the two portions of the column. The more volatile desorbent components are fractionated upward out of the fractionation zones and emerge into the upper portion of column 116. The less volatile raffinate components, e.g., the branched paraffins are concentrated into a bottoms stream and removed from the first fractionation zone via line 120 termed raffinate product. The raffinate product of line 120 is collected.

Concurrently, line 112 delivers the extract stream to a second vertical fractionation zone occupying a large portion of the left-hand side of column 116. The less volatile extract components, the normal pentane and normal hexane, are concentrated into a bottoms stream and removed from first fractionation zone via line 122, the extract product. As with the first fractionation zone, the upper end of the second zone is in open communication with the upper section of column 116 which contains additional fractionation trays extending across the entire column cross section. Desorbent compounds present in the extract stream 112 are driven upward in a second fractionation zone and enters the top of column 116. The top of column 116 is a purification zone which is not intended for the separation of extract or raffinate compounds from the desorbent. This section may be optionally used in the present embodiment to adjust the ratio of normal butane to isobutane to the desired ratio for the adsorbent function. A stream of liquid phase desorbent in the desired ratio of normal butane to isobutane is removed from column 116 and recycled to adsorptive separation section 108 via line 110. A vapor stream comprising desorbent compounds is removed from the top of column 116 via line 128 and passed through an overhead condenser 130 to form liquid desorbent which may be removed from condenser 130 via line 132. A portion of line 132 may be recycled to column 116 for reflux. If no adjustment of the ratio of normal butane to isobutane is desired, a desorbent stream may be removed from the top of column 116. A portion of the desorbent stream may be used for reflux.

Typical operating conditions for column 116 include a pressure in the range of about 0 to about 150 psig, or from about 50 to about 100 psig. Column 116 would typically contain from about 30 to about 80 trays, and specific embodiments may contain from about 40 to about 60 trays. Typical molar reflux ratios range from about 0.5 to about 1.5.

Each of the first and second fractionation zones has independent reboiler systems. For example, the first fractionation zone contains reboiler 124 whereas the second fractionation zone contains reboiler 126. However, the combination of the traditional distillation columns, one for the extract stream and one for the raffinate stream into a single integrated distillation column significantly reduces the necessary capital investment. Specifically, the overhead system for each of the traditional distillation columns is combined into a single overhead system on the integrated distillation column, thereby reducing capital and operational costs.

What is claimed is:

1. An isomerization process having a simulated moving bed adsorptive separation zone and a integrated fractionation zone, said process comprising:

a) contacting, in an isomerization zone, a feed stream containing at least normal pentane and normal hexane with an isomerization catalyst under isomerization conditions to convert at least a portion of the normal pentane and normal hexane into isomerized products and form an isomerization zone effluent containing normal pentane, normal hexane and isomerized products;

b) passing the isomerization zone effluent to an adsorptive separation zone comprising a bed of a selective adsorbent maintained at adsorption promoting conditions under which the normal pentane and normal hexane are selectively retained on a quantity of the selective adsorbent, thus forming a raffinate stream comprising the isomerized products and a desorbent compound formerly present in the quantity of the selective adsorbent;

c) passing a desorbent into contact with said quantity of the selective adsorbent which has retained the normal pentane and normal hexane under desorption promoting conditions to yield an extract stream comprising normal pentane, normal hexane, and the desorbent compound;

d) passing the extract stream into an integrated fractionation column operated at fractionation conditions and divided into at least a first and a second vertical fractionation zones, with each zone having an upper and a lower end located within the fractionation column, with the first and second fractionation zones being in open communication at their upper ends at a first end of the column and with the extract stream entering the fractionation column at an intermediate point of the first fractionation zone;

e) passing the raffinate stream into an intermediate point of the second fractionation zone of the fractionation column;

f) removing an extract product stream from a first end of the first fractionation zone, said first end not being in communication with the second fractionation zone and being located at the second end of the column;

g) removing a raffinate product stream from a first end of the second fractionation zone, said first end not being in communication with the first fractionation zone and being located at the second end of the column; and h) removing a desorbent stream comprising the desorbent compound from the first end of the column.

2. The process of claim 1 wherein the desorbent stream removed from the first end of the column is recycled to the adsorptive separation zone.

3. The process of claim 1 wherein the extract product stream from the first end of the first fractionation zone is recycled to the isomerization zone.

4. The process of claim 1 wherein the desorbent is a mixture of normal butane and isobutane.

5. The process of claim 4 wherein the volume ratio of normal butane to isobutane in the desorbent ranges from about 95:5 to about 80:20.

6. The process of claim 4 further comprising a drag stream withdrawn from the desorbent stream removed from the first end of the column to adjust the volume ratio of normal butane to isobutane to fall within the range of from about 95:5 to about 80:20.

7. The process of claim 1 wherein the isomerized products are selected from the group consisting of 2-methylpentane, 3-methylpentane, isopentane, methylcyclopentane, cyclohexane, 2,2-dimethylbutane, 2,3-dimethylbutane, and combinations thereof.

8. The process of claim 1 further comprising an undivided fractionation section extending from the point of open communication between the first and second fractionation zones to the first end of the fractionation column.

9. The process of claim 8 further comprising withdrawing a side desorbent stream of isobutane and normal butane from the undivided fractionation section at a location so that the range of normal butane to isobutane is from about 95:5 to about 80:20.

* * * * *